United States Patent
Ulbrich et al.

[11] Patent Number: 6,156,045
[45] Date of Patent: *Dec. 5, 2000

[54] INSTRUMENT FOR THE APPLICATION OF SURGICAL MATERIAL

[75] Inventors: Wolfgang Ulbrich, Erding; Roman Carbon, Erlangen, both of Germany

[73] Assignee: Nycomed Arzneinittel GmbH, München, Germany

[*] Notice: This patent issued on a continued prosecution application filed under 37 CFR 1.53(d), and is subject to the twenty year patent term provisions of 35 U.S.C. 154(a)(2).

[21] Appl. No.: 09/077,997

[22] PCT Filed: Dec. 13, 1996

[86] PCT No.: PCT/IB96/01431

§ 371 Date: Feb. 10, 1999

§ 102(e) Date: Feb. 10, 1999

[87] PCT Pub. No.: WO97/21383

PCT Pub. Date: Jun. 19, 1997

[30] Foreign Application Priority Data

Dec. 13, 1995 [DE] Germany ............................ 195 46 434
Dec. 13, 1995 [DE] Germany ............................ 195 46 438
Mar. 18, 1996 [DE] Germany ............................ 196 10 592

[51] Int. Cl.[7] .................................................. A61B 17/00
[52] U.S. Cl. .............................. 606/151; 604/27; 604/36; 604/158; 604/171; 604/264
[58] Field of Search .......................... 606/1, 151; 604/13, 604/15, 60, 264, 286, 27, 36, 171, 158

[56] References Cited

U.S. PATENT DOCUMENTS

| | | |
|---|---|---|
| 4,291,694 | 9/1981 | Chai . |
| 4,796,603 | 10/1989 | Dahike et al. ............................ 128/889 |
| 4,872,456 | 10/1989 | Hasson ...................................... 606/151 |
| 5,137,520 | 8/1992 | Maxson et al. ........................... 604/180 |
| 5,147,374 | 9/1992 | Fernandez ..................................... 606/1 |
| 5,149,387 | 9/1992 | Jansen et al. ................................. 623/1 |
| 5,176,692 | 1/1993 | Wilk et al. ............................... 606/151 |
| 5,195,507 | 3/1993 | Bilweis ........................................ 128/20 |
| 5,256,132 | 10/1993 | Snyders ...................................... 600/16 |
| 5,269,753 | 12/1993 | Wilk .......................................... 604/49 |
| 5,281,197 | 1/1994 | Arias et al. ................................ 604/57 |
| 5,304,187 | 4/1994 | Green et al. ............................. 606/151 |
| 5,310,407 | 5/1994 | Casale ........................................ 604/51 |
| 5,350,387 | 9/1994 | Semm ...................................... 606/151 |
| 5,358,474 | 10/1994 | Kaldany ...................................... 604/57 |
| 5,370,650 | 12/1994 | Tovey et al. ............................. 600/151 |
| 5,387,224 | 2/1995 | Semm ...................................... 606/191 |
| 5,437,636 | 8/1995 | Snoke et al. .............................. 604/95 |
| 5,464,403 | 11/1995 | Kieturakis et al. ...................... 606/151 |
| 5,503,623 | 4/1996 | Tilton, Jr. ................................. 606/151 |
| 5,919,184 | 7/1999 | Tilton, jr. ................................. 606/151 |

FOREIGN PATENT DOCUMENTS

| | | |
|---|---|---|
| 2 090 000 | 8/1993 | Canada . |
| 0 059 265 | 9/1982 | European Pat. Off. . |
| 0 160 870 | 11/1985 | European Pat. Off. . |
| 0 411 767 | 2/1991 | European Pat. Off. . |
| 0 535 508 | 4/1993 | European Pat. Off. . |
| 0 543 499 | 5/1993 | European Pat. Off. . |
| 0 557 964 | 9/1993 | European Pat. Off. . |
| 581036 | 2/1994 | European Pat. Off. ........ A61B 17/00 |
| 557963 | 4/1994 | European Pat. Off. ........ A61B 17/00 |

(List continued on next page.)

Primary Examiner—Gary Jackson
Attorney, Agent, or Firm—Wenderoth, Lind & Ponack, L.L.P.

[57] ABSTRACT

The present invention relates to an instrument for the application of material and comprising an elongated unit, a material application member pivotally connceted to the distal end of the elongated unit, so as to allow movement of an applicating member relative to the elongated unit, means for retaining the applicating member in a desired angular positon during surgical intervention. In particular, an instrument according to the invention is suited for the application of surgical sheet repair material. An instrument according to the invention is designed for use in minimally invasive, endoscopic or conventional surgery.

28 Claims, 9 Drawing Sheets

FOREIGN PATENT DOCUMENTS

| | | |
|---|---|---|
| 592243 | 4/1994 | European Pat. Off. ........ A61B 17/28 |
| 0 750 885 | 1/1997 | European Pat. Off. . |
| 84 26 364.4 | 9/1986 | Germany . |
| 38 25 631 | 2/1990 | Germany . |
| 41 32 855 | 4/1993 | Germany . |
| 92 16 838.8 | 4/1993 | Germany . |
| 41 38 100 | 5/1993 | Germany . |
| 43 00 307 | 7/1994 | Germany ....................... A61B 17/28 |
| 295 08 254 | 11/1995 | Germany . |
| 92/06638 | 4/1992 | WIPO ........................... A61B 17/00 |

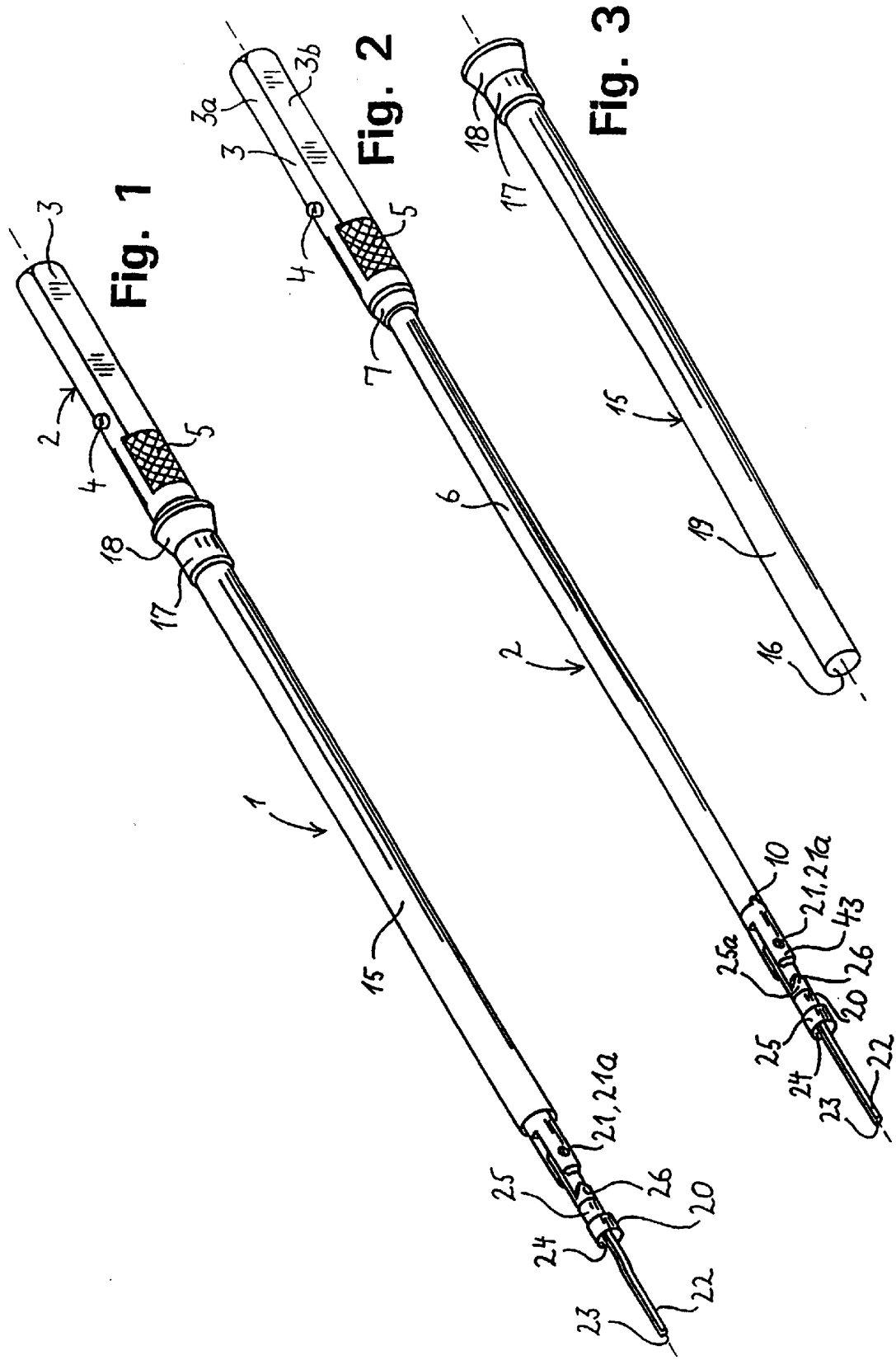

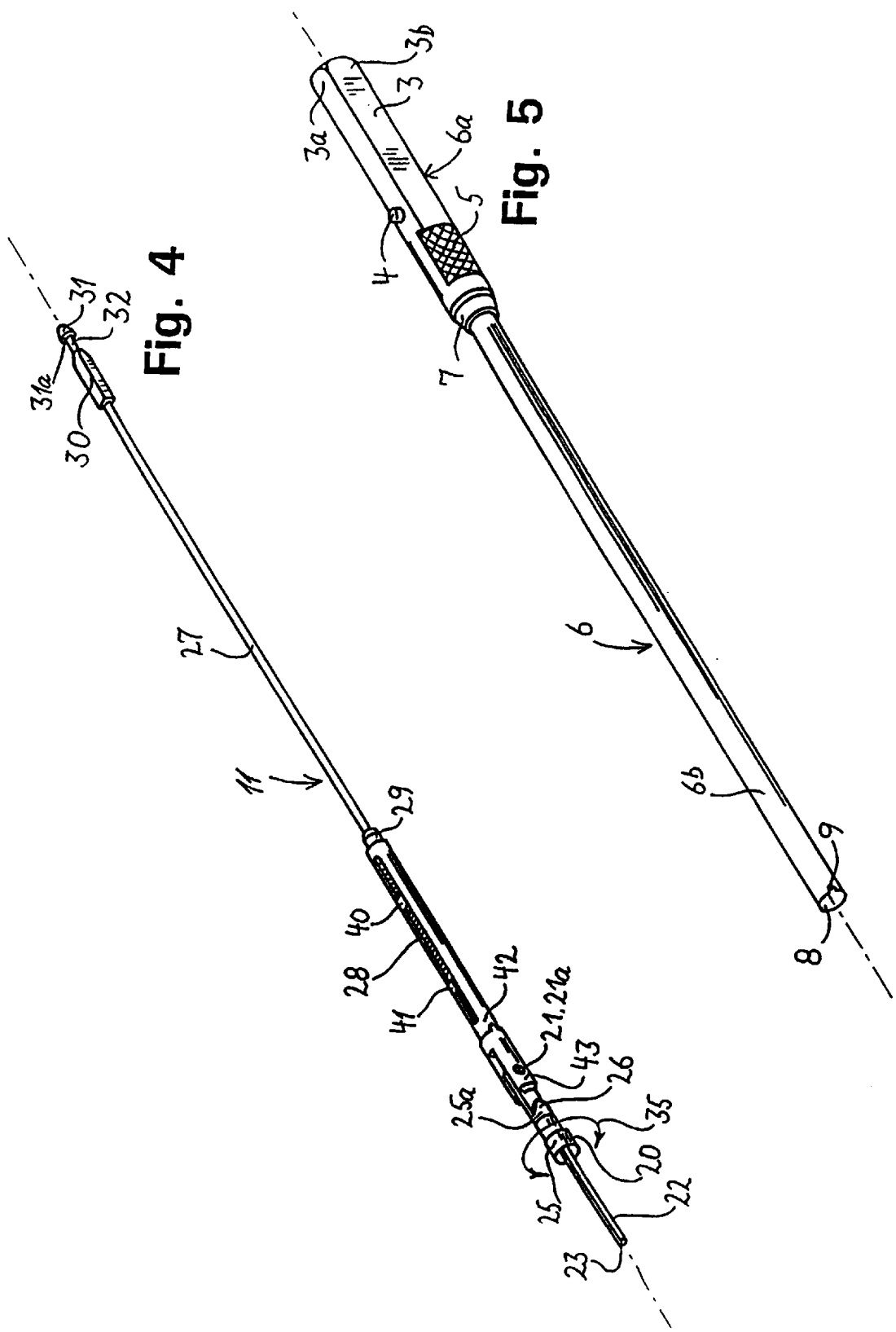

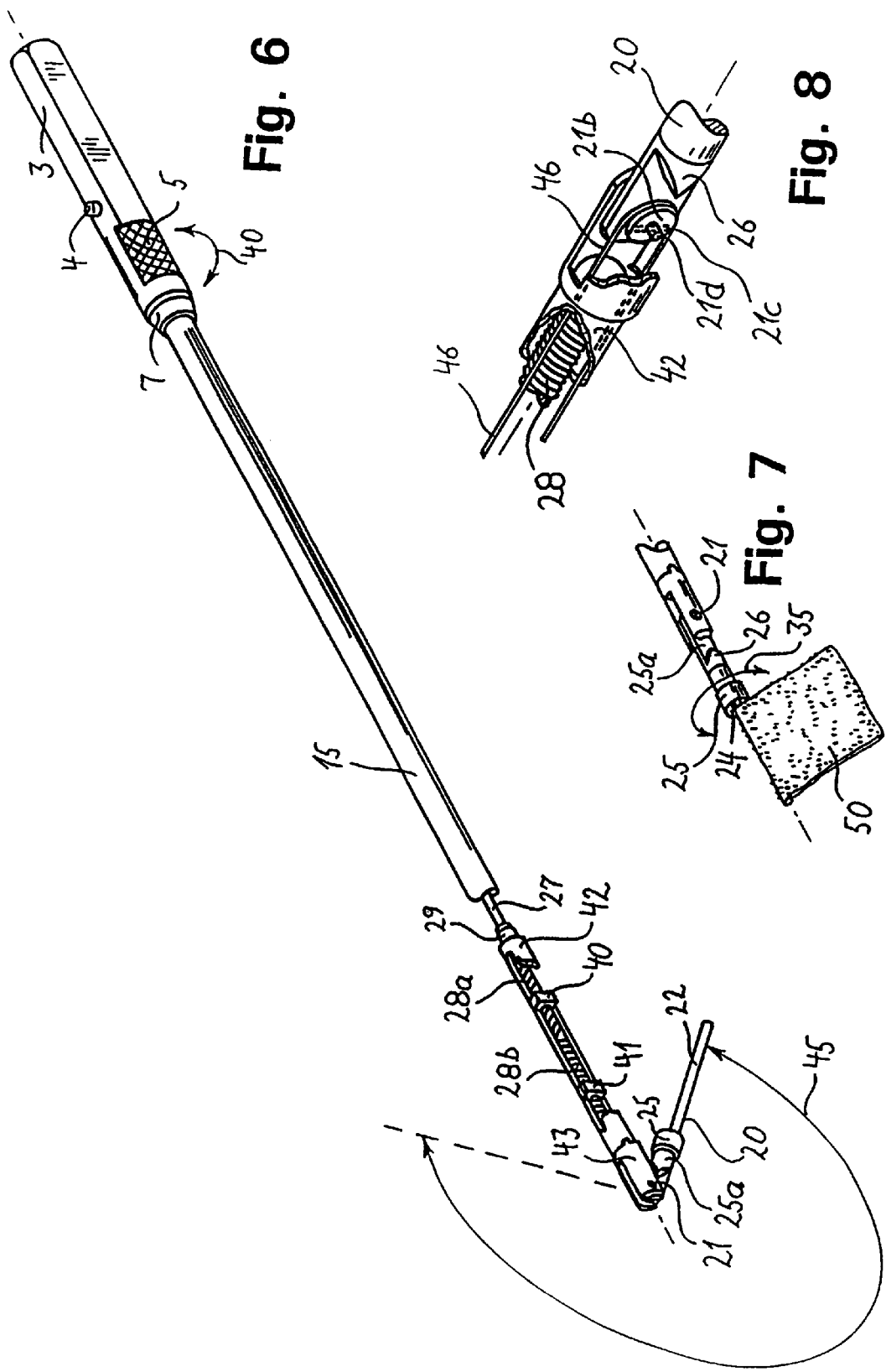

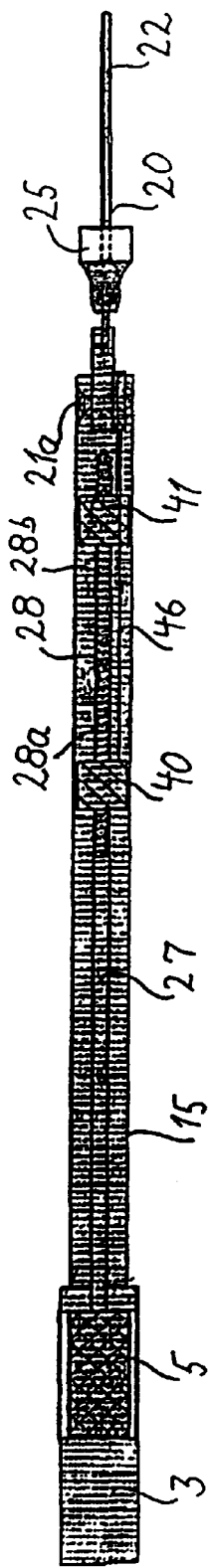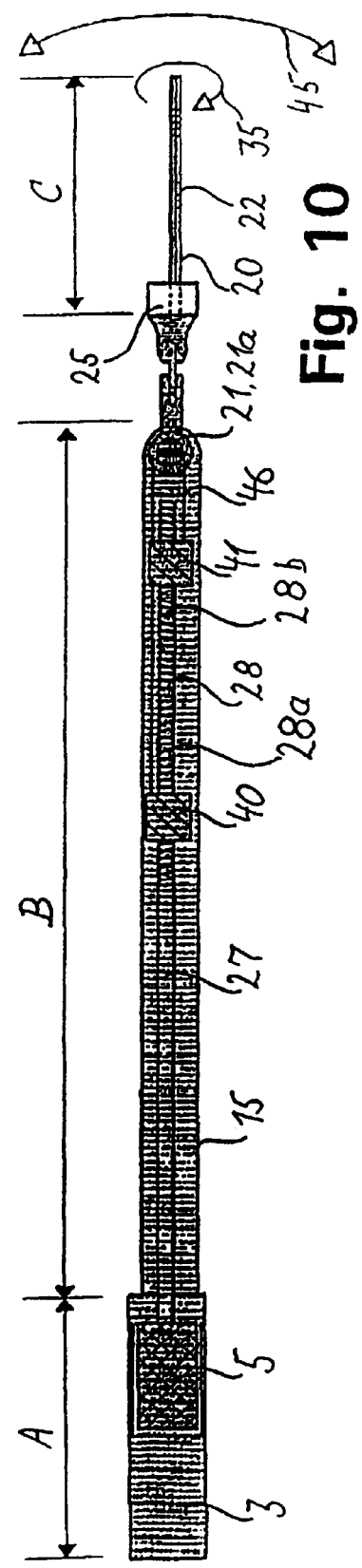

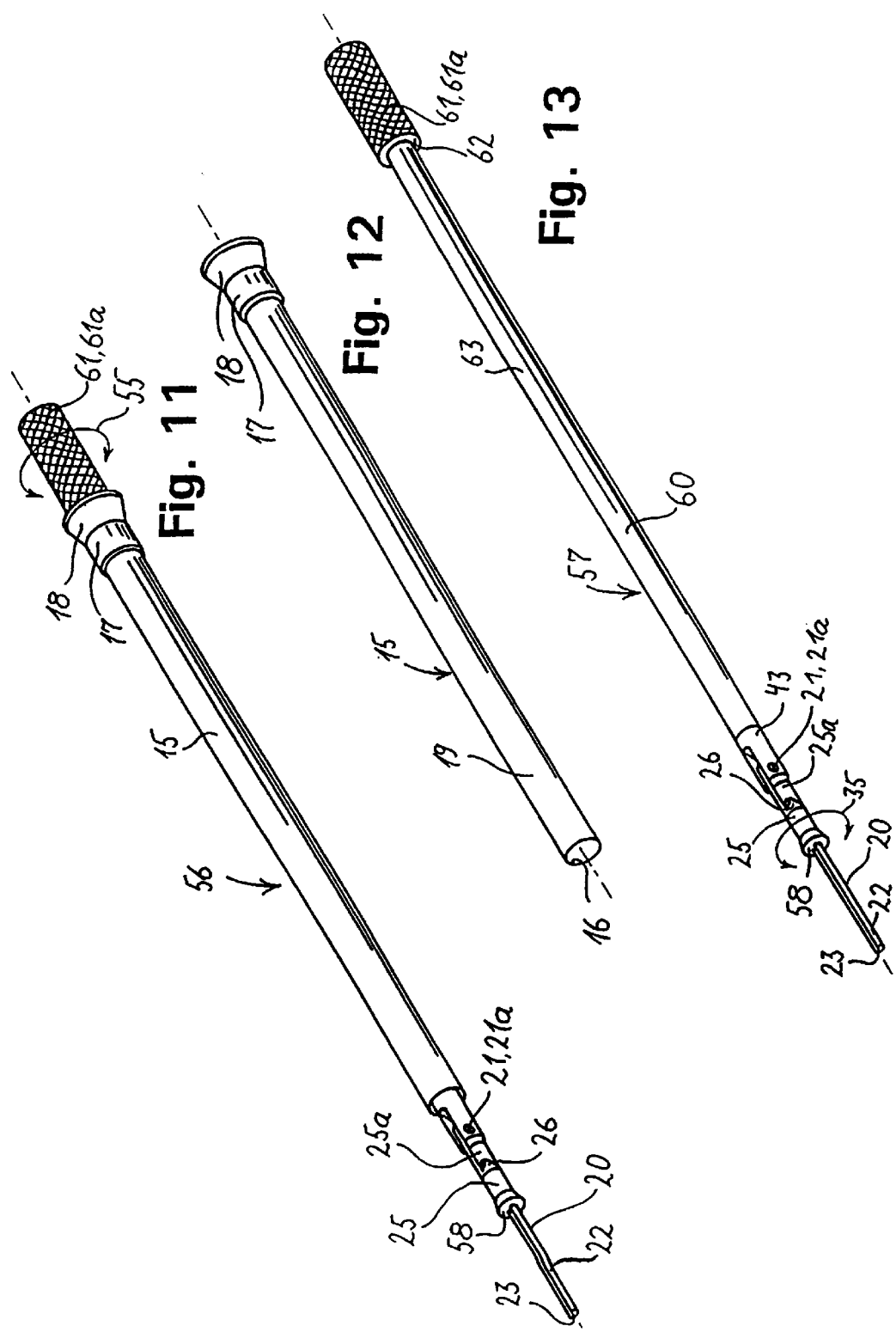

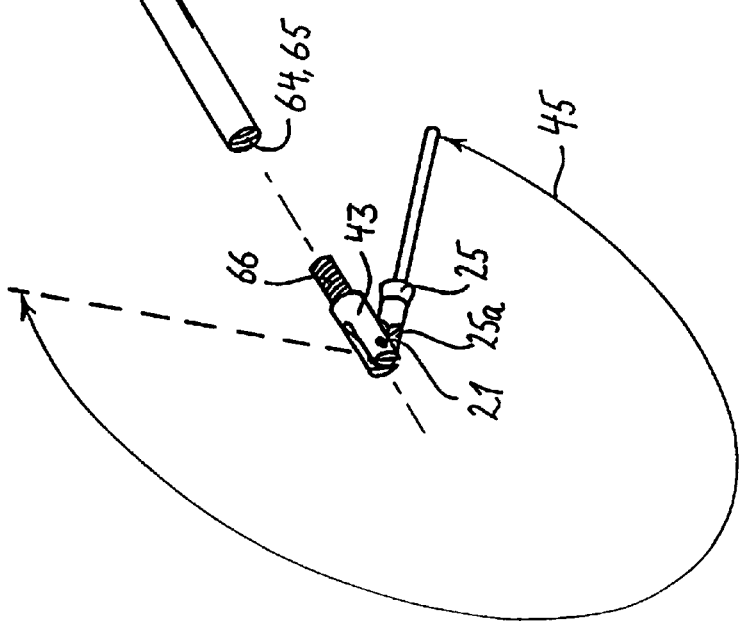

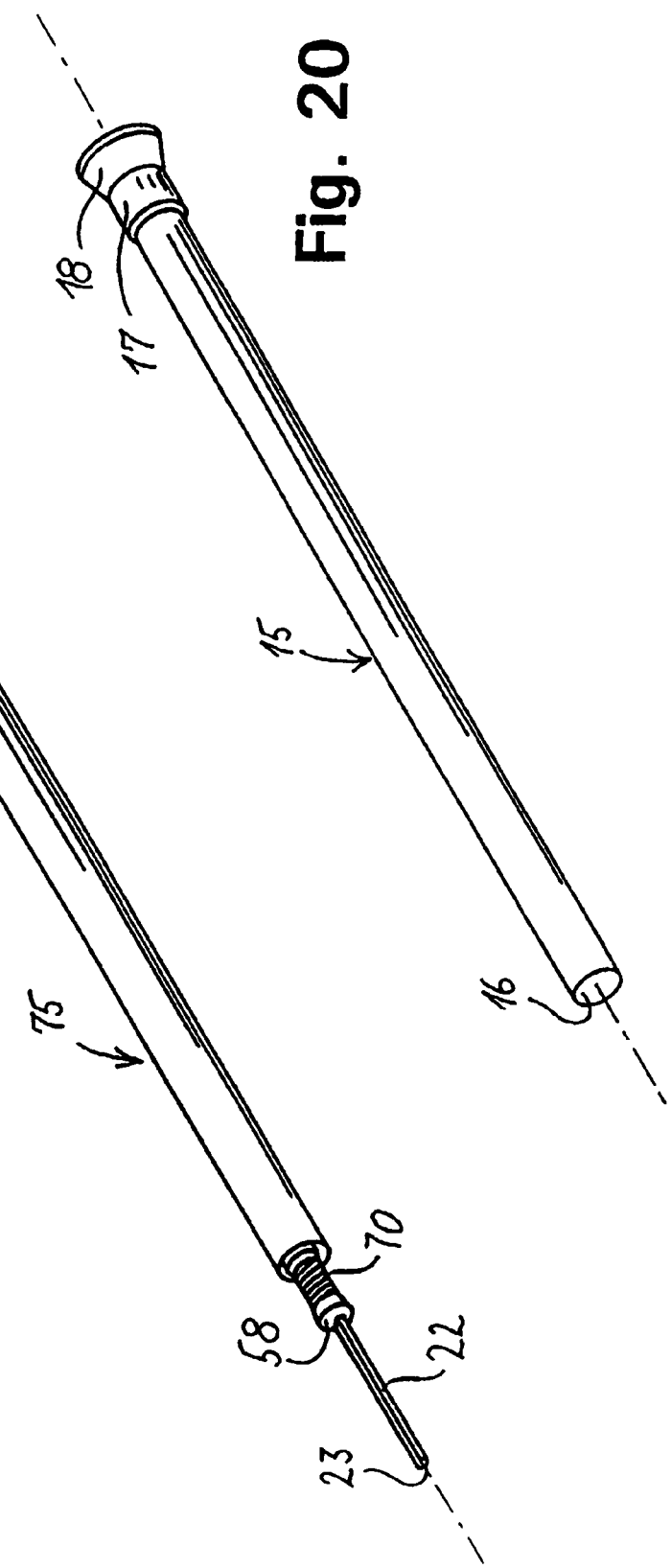

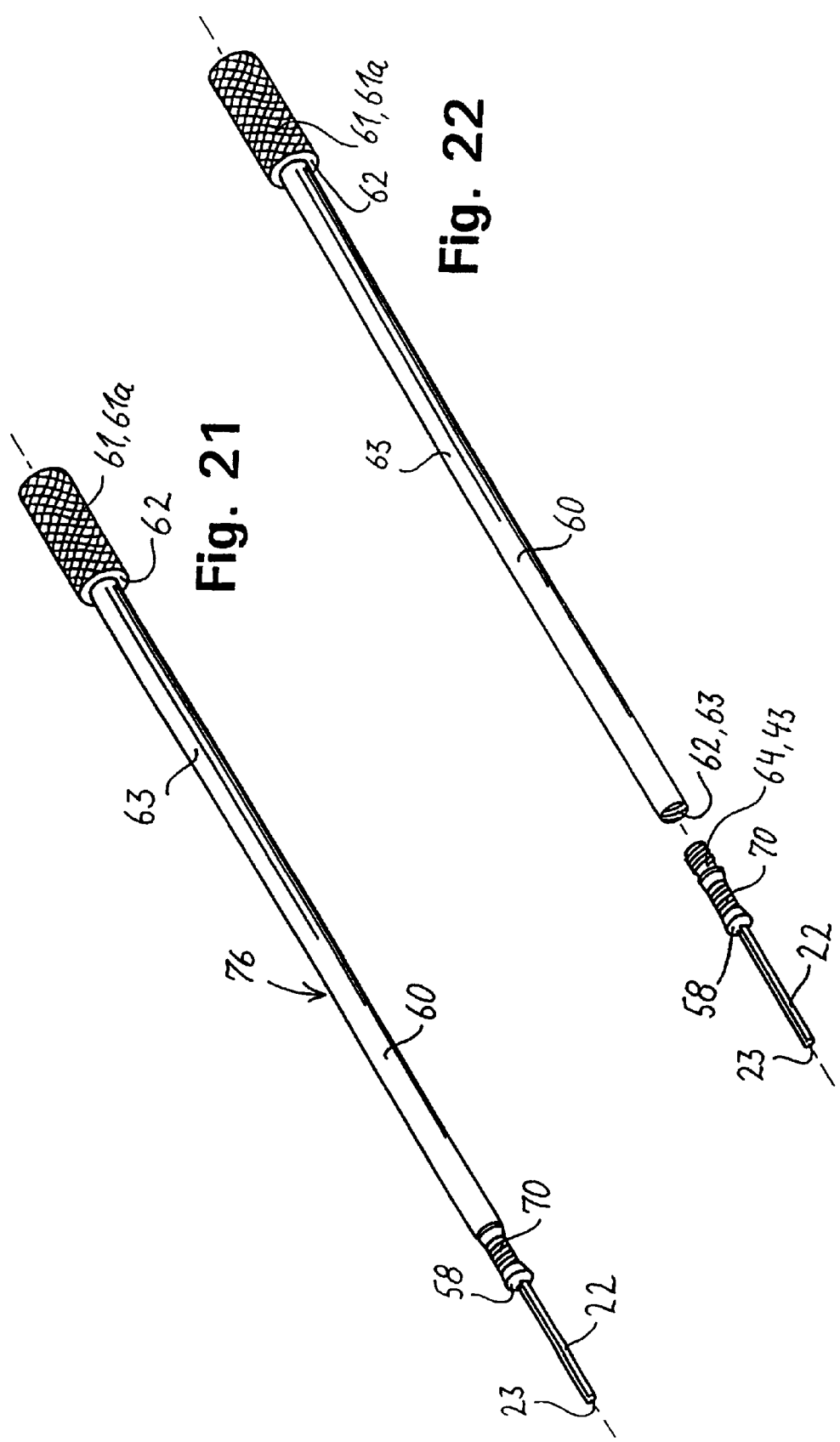

200~# INSTRUMENT FOR THE APPLICATION OF SURGICAL MATERIAL

BACKGROUND OF THE INVENTION

The present invention relates to an instrument for the application of a surgical material. The instrument has been developed for use in surgery, especially in the so-called minimally invasive surgery, and is suitable for use in connection with an application of a surgical material such as, e.g., a wound-healing material or a material adapted for stopping or reducing bleeding during or after an operation.

As indicated above, an instrument according to the present invention is intended for use in any kind of surgery involving application of a surgical material. However, the instrument has been developed especially with the aim of developing an instrument which also is suitable for use in minimally invasive surgery. The concept "minimally invasive surgery" was originally named by Wickham in 1987 and means that ordinary, conventional operation is performed through small orifices. The term "minimally access surgery" has also been used for minimally invasive surgery, since the orifice is indeed minimal, however, the actual operation naturally corresponds to the ordinary operation method.

Minimally invasion in the human body has been a research object for many decades. The invention of simple optical instruments considerably improved diagnosis of disorders related to internal parts of the body. In the beginning of the 50s, the optical instruments were markedly improved by means of new rod lens systems and formed the basis for the development of endoscopic methods. In particular, endoscopy is suitable for use in nearly every medical speciality such as, e.g., in internal medicine, gynaecology, urology, neurosurgery, ORL (oto-rhino-laryngology) and surgery.

In terms of surgical intervention in a body cavity, minimally invasive procedure means that the body cavity in question, e.g. the chest or the abdominal cavity, is opened via a trocar and a lens is introduced. The same applies to thoracoscopy or laparoscopy. Depending on the necessary tools, trocars can have different diameters. For the time being 1.7 mm, 3, 5, 8 and 10/12 mm are the most common. Over the past years, the tendency to minimize the diameter of the trocars has progressed so that today many operations are partly performed by means of so-called "needle instruments" with a diameter of 1.7 mm.

The tools used in conventional surgery have been "transferred" to the minimally invasive surgery techniques. All ordinary forceps, clips or scissors can be obtained as corresponding long-handled instruments. Also high-frequency coagulation, laser and clip sewing instruments (staplers) have been tailor-made for the minimally invasive surgery.

An important tool in the minimally invasive surgery is also fibrin adhesives which are important for tissue management. For the application of such adhesives, rigid and flexible double lumen hollow needles were developed by the present inventors for liquid adhesion. As something new, spray adhesion is also possible in minimally invasive surgery. A very advantageous surgical material for use in traditional surgery as well as in minimally invasive surgery is a material called TachoComb® which is manufactured by Nycomed Austria GmbH and which is a fibrin glue-impregnated fleece (BP-B-0 059 265). After introducing TachoComb® material into conventional surgery, the use of this important contribution to surface management also in the field of minimally invasive surgery has turned out to be most helpful. As minimally invasive surgery stitching methods are very costly and often do not meet the surgical requirements, the particular properties of a fleece-adhesive like TachoComb® seem to be very advantageous in the field of minimally invasive surgery TachoComb® has indeed proved to be a very useful and beneficial tool in any kind of surgical intervention. Tests concerning liquid adhesion employed in minimally invasive surgery have shown that with regard to capacity, indication width, and reliability, the advantages of a fleece-bound fibrin adhesive have been far from reached. In minimally invasive surgery, intracorporal coating of a carrier with fibrin adhesive, as it is conventionally often performed, is not contemplated, as the handling would be too time-consuming and uncertain. An extracorporal self-coating followed by a trocar passage is also dropped, as this would result in huddling of the fleece due to the folding of the carrier material. The fabrication of TachoComb® as a ready-to-use product in dry condition therefore seems to be the choice for minimally invasive surgery application.

The introduction of TachoComb® in the minimally invasive surgery has been very advantageous. After application, the TachoComb® material resides as an internal biodegradable plaster and it is useful as a styptic agent as well as for tissue compression, tissue sealing and tissue healing. The TachoComb® material has made a remarkable contribution to surgery as operations which previously would have been inconceivable or impracticable are now made possible through the application of TachoComb® (or the like). An example is the application of TachoComb® in the case of pneumothorax. In the following, TachoComb® material is used as an example of a surgical material. It is of course within the scope of the invention that other surgical materials than TachoComb® may be applied by use of an instrument according to the invention.

The application of a surgical material like e.g. TachoComb® during minimally invasive surgery can be made without any specialized equipment. Originally, TachoComb® was used tightly rolled up in its ordinary size of 9.8×4.8 cm along a short distance resulting in a kind of carpet roll with a diameter of 10 mm and a length of 50 mm. This roll was extracorporally introduced in a 10/12' trocar sleeve. In a trocar pre-perforation into the body cavity in question, the thus armoured trocar sleeve could now be introduced, the TachoComb® roll could be "stamped out" by means of the trocar pin and be taken over by forceps for further positioning and application.

This method is no doubt practicable, however, combined with obstacles due to the fact that i) a further trocar is necessary, ii) when introducing a fresh trocar sleeve armoured with TachoComb®, wound secretion can be pressed into the sleeve and may, thus, activate the adhesive too soon, iii) the handling of the fleece-roll with two forceps for positioning and final application requires a high degree of handiness and endurance as every unintended tissue contact will result in activation and make the rolling-up of the roll difficult and impossible, respectively, and iv) a "modelling" of the fleece under tension onto the parenchyme surface by the use of two forceps is difficult, as the fleece pulls out under too heavy tension.

In order to overcome at least some of the above-mentioned disadvantages, the ENDOdock® applicator was developed (EP-A-0 750 865). This applicator is especially designed for application of relatively small sized surgical material (such as, e.g., 3×2 cm). A pleural sealing using the ENDOdock® applicator, e.g. in the case of pneumothorax, is more difficult to thoracoscopy, as, due to an enormous surface tension, the stability offered by the fleece is not sufficient. The same applies to laparoscopy when dealing with a liver or spleen rupture where a larger adhesive surface must also be available. Indications for sealing of the gallbladder's bed at the liver, where at least in regard to the size, an effort might be contemplated, are rare, as bleedings and small gall leaks will coagulate easily.

Moreover, the ENDOdock® system has some deficiencies with regard to a reliable application in that; i) the plastic screen does not always unfold sufficiently effectively, especially if it has been in the applicator for several minutes; ii) stripping of the fleece may be difficult as the adhesive strength of the adhesive can be lower than the strength of the fleece-holding device; and iii) in some cases, the plastic screen may work loose from the applicator and will only be found in the body cavity with difficulty (not X-ray detectable, transparent).

As it appears from the above, there is a demand for the development of an instrument for the application of a surgical material, notably a material like TachoComb®, during surgery especially during minimally invasive surgery without one or more of the above-mentioned problems. An object of the present invention is therefore such a novel instrument. The development of an instrument according to the invention is based on the following optimal requirements for such an instrument:

1. The applicator should be suitable for application of surgical material having a small as well as a large size.
2. For physical reasons (tear strength, shear stress), the applicator should ensure that all the surgical material can be used.
3. The applicator should be flexible in its movements.
4. The surgical material (e.g. as a fleece-roll) should be able to be manipulated to hardly reached regions.

An instrument according to the invention is advantageous with respect to at least one or more of the above-mentioned requirements compared with the prior art (e.g. ENDOdock® applicator).

The present invention provides an instrument for the application of surgical material fulfilling at least some of the above mentioned requirements. More particular, the present invention provides an instrument for the application of surgical material and comprising an elongated unit, a material applicating member pivotally connected to the distal end of the elongated unit, so as to allow movement of the applicating member relative to the elongated unit, and means for retaining the applicating member in a desired angular position during surgical intervention.

The major advantage of the instrument according to the invention over prior art instruments, in particular those of U.S. Pat. No. 5,147,387 and U.S. Pat. No. 5,370,650, is that it allows intracorporal manoeuvring of the applicating member while, at the same time, it may be retained in any position within the range of its movement. This both facilitates the handling of the instrument, and makes the surgical intervention more safe, as the applicating member will not perform an uncontrolled movement when returning to its original position.

The means for retaining the instrument in an angular position during surgical intervention may comprise mechanical means and/or magnetic means, including electromagnetic means. The mechanical means may comprise a friction hinge connection interconnecting the applicating member and the elongated unit and/or mechanical locking means, such as spring loaded locking means, means locking by engagement between two or more mechanical parts or any other means for retaining the applicating member in a desired position. The magnetic means may comprise permamagnets as well as electromagnets permanently activated or electromagnets activated by electrical signals from an extracorporeal position. The angular range of the applicating member may be infinitely variable, or a finite number of steps in the angular direction or directions may be predefined, e.g., by friction means, spring loaded means, magnetic means etc.

The elongated unit may comprise any kind of means for manoeuvring and/or controlling the instrument, in particular the applicating member, as well as force transmitting means for transmitting the extracorporeal operating movements to the applicating member, means for holding and handling the instrument, proofing means for avoiding gasses or liquids to ooze out of the body of the patient during minimally invasive surgery, means for applying surgical material, including air and liquids, to the surgical area during surgical intervention, signal transmitting means in case of sensing devices or additional surgical devices are positioned on the instrument.

More particular, the present invention relates to an instrument, wherein the applicating member comprises a rod-shaped portion so as to allow a sheet of surgical material such as, e.g., TachoComb® to be rolled up to form a carpet-like roll of surgical material on the rod-shaped portion of the applicating member. The rod-shaped portion may further comprise sensing devices and/or any other optional devices useful during surgical intervention.

At least the rod-shaped portion of the applicating member may further define a slit extending longitudinally over at least part of the length of the applicating member, so as to provide a cavity for anchoring a surgical material, e.g., TachoComb®. Other mechanical means for anchoring the surgical material are possible, friction means, spring loaded or other force loaded mechanisms, as well as means where an adhesive effect of the surgical material such as, e.g., TachoComb® is used for retaining the material on the rod-shaped part of the elongated member.

The invention further relates to an instrument comprising a first sleeve member having a bore allowing the applicating member and at least the distal portion of the elongated unit to pass therethrough. The sleeve member is adapted to be received in a trocar during surgical intervention, but the instrument may also be employed in surgical interventions where no trocar is used. The sleeve member, which preferably may have a tube-like form with a through-going bore in its longitudinal direction, preferably has an outer diameter fitting the sizes of standard trocars. At least a portion of the elongated unit is surrounded by the sleeve member during surgical intervention, while the applicating member and at least the proximal part of the elongated unit is not surrounded by the sleeve member. Handle and/or manoeuvring means and/or other means may be positioned at the proximal end of the elongated unit, as will be further described below.

Preferably, but not mandatory, a radial abutment surface is defined within the bore of the first sleeve member for cooperating with a corresponding abutment surface defined on the elongated unit so as to allow easier control of the elongated unit during surgical intervention. When introducing an instrument according to the invention into the body of a patient through a trocar and while positioning and unrolling the surgical material, the abutment surface defined on the elongated unit may abut the surface defined within the bore of the first sleeve member, whereby an accurate and safe control of the longitudinal displacement of the instrument is obtained.

Though the abutment surface defined in the bore of the sleeve member may have any shape such as a polygonal or a curved shaped, it preferably is an-annular abutment surface having an inner diameter increasing in the direction of the proximal end of the sleeve member. Preferably the annular abutment surface is positioned adjacent to the proximal end of the sleeve member. However, dependent on the specific use of the instrument according to the invention, it may also be positioned any where else within the length of the sleeve member.

A first preferred embodiment of an instrument according to the invention concerns an instrument, wherein the applicating member is pivotal about one axis only. Though this might seem like a limitation in the mobility of the applicating member, this feature in fact establishes a great advantage compared to prior art instruments having pivotally mounted applicating means. As the instrument as such and thereby both the sleeve member and the elongated unit may rotate about their longitudinal axis, the plane of the pivoting movement of the applicating member may be rotated 360° around the axis of the elongated unit, whereby the range of the applicating member becomes three-dimensional. At the same time, the instrument according to the invention may have a well-define pivoting point, whereby its manoeuvring and control becomes easier, more accurate and safe than the manoeuvring and control of instruments having no well-defined pivoting point. Thus, a cheap, easy-to-use system comprising a very limited number of parts is obtained. Obviously, many other configurations, wherein the pivoting movement of the applicating member is not restricted to one plane are possible, e.g, configurations comprising one or more ball-and-socket joints, elastic members interconnecting the applicating member and the elongated unit, as well as configurations allowing pivoting movements in a restricted number of planes.

The instrument according to the invention may further comprise manoeuvring means for the pivotal movement of the applicating member, and operating means operating the manoeuvring means positioned at the proximal end of the elongated unit. Though it is possible to manoeuvre the applicating member by means of other tools, such as forceps, e.g., introduced via other trocars, the manoeuvring and control of the applicating member is made considerably easier and more accurate by providing manoeuvring means for the pivotal movement of the applicating member. The manoeuvring means may comprise force transmitting mechanical means, such as a Bowden cable, one or more worm wheels, a rack/toothed wheel configuration, a system of stiff rods, a wire system, a spindle/nut configuration and/or combinations thereof or any other mechanism. The mechanical means may be activated by hand or they may be combined with electrical activation means, such as an electromotor.

Preferably, the elongated unit comprises an elongated rod member on which the applicating member is mounted and a second sleeve member surrounding the rod member and having a handle formed at its proximal end. The surrounding second sleeve member may have several functions. The handle formed at the proximal end of the sleeve member allows the operator to handle the instrument in a secure and safe way. Further, the second sleeve member, preferably having a smooth and straight outer surface, protects any manoeuvring or other means extending from the applicating member to the distal end of the elongated unit, and at the same time it stabilises the elongated unit when introducing it into a trocar.

Preferably, the abutment surface of the elongated unit is formed at the distal end of the handle in order to minimize material costs.

The manoeuvring means for manoeuvring and controlling the applicating member preferably comprise force transmission means interconnecting the operating means and the applicating member. While the operating means are positioned at an extracorporal position, the applicating member is positioned at an intracorporal position at a considerable distance from the position of the operating means. As described above, the force transmitting means may comprise different kinds of configurations.

In order to allow the instrument to be disassembled for it to be effectively cleaned and sterilized, the operating means may be releasably connected to the manoeuvring means. This further facilitates mechanical maintenance of the instrument.

Though many configurations of an instrument according to the invention are possible as mentioned above, a preferred embodiment thereof relates to an instrument, wherein the operating means comprise a rotatably mounted adjustment member, the manoeuvring means being adapted to transform a rotating movement of the adjustment member into a rotating movement of the applicating member around its pivot at the distal end of the elongated unit. As it is aimed to provide an accurate and easy control of the pivoting movement of the applicating member, a preferred embodiment of the invention comprises an operating member comprised in the handle and being rotatably mounted therein. Other configurations are possible, e.g., configurations wherein the handle is mounted at a distance from the handle, and configurations where the operating members are operated by linear activating movements. However, the rotating activating movement is preferred as it provides a compact design of the instrument.

As mentioned above, the manoeuvring and force transmitting means may comprise different mechanical systems. In the most preferred embodiment of the instrument, the force transmission means comprise a spindle, which is mounted rotatably about its longitudinal axis and coextend with the rod member, and which has first threads formed thereon, and at least a first longitudinally displaceable member defining second threads engaging with the first threads, the displaceable member being interconnected with the applicating member, whereby rotation of the spindle member causes displacement of the first displaceable member and a pivoting movement of the applicating member. The use of a rotatable spindle and one or more longitudinally displaceable members provides a mechanism for transforming the rotating movement of the operating means and thereby of the spindle into a linear movement, which again may be transformed into a pivoting movement around an axis perpendicular to the rotational axis of the spindle.

Preferably, the force transmission means further comprise third threads formed on the spindle, the first and third threads being right and left handed, respectively, or vice versa, and a second displaceable member defining fourth threads cooperating with the third threads and being interconnected with the applicating member. By interconnecting the two displaceable members by a stretched wire forming at leat one close loop around a pivoting sleeve of the applicating member at the distal end of the elongated unit, the applicating member may be pivoted around its pivot by displacing the displaceable members. Thereby the straight portions of the wire performs a linear movement, while the looped portion of the wire performs an angular movement causing the applicating member to pivot, as at least part of the wire loop engage with the pivoting sleeve of the applicating member. Because the wire is stretched between the two displaceable member, which are provided with counterdirected threads engaging with corresponding threads on the spindle, the wire will be subjected to tension irrespective the direction of the rotational movement of the spindle and the direction of the linear movement of the displaceable members.

Though the above description covers a preferred embodiment of the invention, other operating and manoeuvring means are possible, cf. the earlier description thereof.

Preferably, the elongated rod member is mounted rotatably about its longitudinal axis in relation to the handle, the spindle being mounted on or forming part of the rod member.

In order to facilitate unrolling of a sheet of surgical material during surgical intervention, at least the rod-shaped part of the applicating member is mounted rotatably about its longitudinal axis about a non-rotatable, proximal part of the applicating member.

A particular embodiment of an instrument according to the invention further comprises a sleeve member having a trumpet-shaped enlargement at its proximal end, and wherein the elongated unit comprises a shaft with a handle. The interconnection between the elongated unit and the applicating member may comprise a contact member, which is movable connected to the elongated unit, and which may pivot at an angle of up to about 135° to each side from its straight position, and which is connected to the elongated unit by means of a tension bolt, and wherein the contact member comprises connection means, which are guided through the elongated unit to the upper exterior of the first portion of the elongated unit. Further, the applicating member with a stopping means and a sheet holding means is pivotally connected to the contact member.

It should be understood that the above description of an instrument only covers one of many possible specific embodiments within the scope of the invention. As mentioned earlier, other possible embodiments are instruments, wherein the connection means comprise a toothed wheel or a worm wheel, a Bowden cable and/or a chain cable as well as the above mentioned configurations. Further the angular range of the pivoting movement of the applicating member mentioned above should be understood only as an example and as one of more preferred possible angular ranges.

A second embodiment of the invention relates to an instrument, wherein the elongated unit has at least a proximal and a distal portion, the cross section of the proximal portion being greater than the cross section of the distal portion, so that an abutment surface is formed, and the proximal portion forms a handle, and wherein at least the rod-shaped part of the applicating member is mounted rotatably about its longitudinal axis about a non-rotatable, proximal part of the applicating member. This second specific embodiment of the invention comprises no operating means for operating the pivoting movement of the applicating member. The pivoting movement is preferably activated by catching the applicating member or the surgical material by other tools, such as forceps, which during minimally invasive procedures are introduced through other trocars. The pivotal interconnection between the applicating member and the elongated unit may be obtained by any of the means described above.

The second preferred embodiment of the instrument according to the invention further comprises a first sleeve member identical to the one described above. The first sleeve member preferably further has a trumpet-shaped enlargement at its proximal end. The elongated unit may comprise shaft with a handle, and the interconnection between the elongated unit and the applicating member may comprise a contact member, which may pivot at an angle of up to about 135° to each side from its straight position. The tensile strength of the hinge mechanism, i.e., the force required to activate the pivoting movement of the applicating member may be determined by the distortion of a tension bolt. The applicating member may comprise a stop screw, and a sheet holding means may rotatably mounted on the contact member.

The force required in order to activate the pivoting movement of the applicating member may be determined by other means than a tension bolt, e.g., by a spring and/or by other mechanical means and/or by magnetic means. The stop for the pivoting movement of the applicating member is optional, however means clearly defining the angular range of the pivoting movement of the applicating member are desired in order to obtain an optimal control the applicating member during surgical intervention. This applies not only to the second preferred embodiment of the invention, but to all preferred embodiments.

Further the angular range of the pivoting movement of the applicating member mentioned above should be understood only as an example and as one of more preferred possible angular ranges.

In a further aspect, the invention relates to an instrument for the application of surgical material and comprising an elongated member, a material applicating member pivotally connected to the distal end of the elongated member, wherein the elongated member has at least a first and a second portion, and wherein the second portion is surrounded by a sleeve member, and wherein the interconnection between the elongated member and the applicating member has an extension forming the applicating member, said extension being provided with a slit, the alit being suited for fastening a sheet of surgical material, the applicating member being pivotable at an angle of up to about 90° in any direction.

The applicating member preferably has the same characteristics as described above, while the sleeve member preferably has the characteristics of the first sleeve member as described above. The first portion of the elongated member preferably forms a handle, and preferably the cross section of the first portion is greater than the cross section of the second portion. The cross sectional extension between the second and the first portion preferably forms an abutment surface for abutting the abutment surface comprised in the proximal end of the sleeve member.

A specific embodiment of the invention further relates to an instrument, wherein the interconnection between the applicating member and the first elongated member comprises a spiral spring.

The spiral spring establishes a pivotable link between the applicating member and the elongated member. The spiral spring allows the applicating member to pivot in any direction into a position, where the free end of the rod-shaped portion of the applicating member hits the first elongated member, or into any intermediate position. The pivoting movement of the applicating member 20 may be activated by hand using other tools, e.g., forceps. The force needed to activate the pivoting movement of the spring is determined by its spring constant.

In other embodiments of the invention, the spiral spring is substituted by any elastic member, e.g., a solid member made from a resilient material.

In a more specific embodiment of the invention, the free end portion of the spiral spring may form at least part of the second elongated member. Though this a possible configuration, it is not a preferred embodiment, as it requires a thick spring wire compared to the thickness of the applicating member, whereby the spring becomes too stiff or whereby the applicating member becomes to weak.

As described in the introduction an instrument according to the invention is suitable for use in connection with application of a surgical material, preferably in connection with surgical intervention such as minimally invasive surgery. In this connection, a surgical material of particular importance is TachoComb®.

The TachoComb® material is primarily used for the sealing of body tissue. The possibilities within the minimally invasive surgery comprise e.g. selective sealing of parenchyme organs (lungs, liver, spleen, kidneys), organs like the gastrointestinal tract and the urogenital tract and structures like the lymphoglandular system, the spinal cord, and the nerves. Due to the characteristics of TachoComb®, an effective imperviousness to all body fluids (blood, lymph, gall, urine) as well as gases will exist after application. By using an instrument according to the invention, both elective surgery (e.g. Hodgkin-Staging) and emergency surgery (e.g. pneumothorax, splenotomy) may be performed by TachoComb® application in minimally invasive surgery.

The benefit to the patient when using this method is significant. Minimally invasive surgery itself reduces the need for analgesics and the period of hospitalisation of the patient. Infections are minimized as the surface area exposed to surgical intervention is reduced, and cosmetic advantages are obtained. By combining minimally invasive surgery with the application of TachoComb®, these effects become more evident, and safe management of body tissue for blood sealing and imperviousness of resection areas are obtained.

Furthermore, due to reduced secretion with a reduced rate of infection, fewer drainage days is a further result of the application of TachoComb® by minimally invasive surgery in patients suffering from cystic fibrosis.

As it is apparent from the above, an instrument according to the present invention is suitable for use in surgery in connection with application of a surgical material. The instrument may be employed in all relevant types of operations, notably operations involving minimally invasive surgery. As an example, in connection with thorax drainage for cystic fibrosis patients, the post-operative drainage period is reduced to an average of 11 hours (compared with an average drainage period of 17 days when traditional drainage is employed). Furthermore, the patients recovered quicker resulting in a shorter hospitalisation time and the degree of hospital-related infections were reduced.

The invention, in particular preferred embodiments thereof, will now be further described with reference to the drawings, wherein:

BRIEF DESCRIPTION OF THE DRAWINGS

FIG. 1 shows an assembly of a first preferred embodiment of an instrument according to the invention, FIG. 2 shows the assembly of FIG. 1, where the first sleeve member is removed, FIG. 3 shows a first sleeve member according to the invention suited for fitting in a trocar, FIG. 4 shows an inner assembly of the first preferred embodiment of an instrument according to the invention, FIG. 5 shows a second sleeve member of an instrument according to the invention, FIG. 6 is a view showing the function of the pivoting movement of the applicating member and the rotating movement of the handle in the first preferred embodiment of the invention, FIG. 7 shows a detail of the applicating member according to the invention and a sheet of surgical material, FIG. 8 shows a detail of the interconnection between the applicating member and the manoeuvring means in the first preferred embodiment of the invention, FIG. 9 is a diagrammatic top view illustrating the working principle of the first preferred embodiment of the instrument according to the invention, FIG. 10 is a diagrammatic side view illustrating the working principle of the first preferred embodiment of the instrument according to the invention, FIG. 11 shows an assembly of a second preferred embodiment of an instrument according to the invention, FIG. 12 shows a first sleeve member according to the invention suited for fitting in a trocar, FIG. 13 shows the assembly of FIG. 11, where the sleeve member is removed, FIG. 14 is a view showing the function of the pivoting movement of the applicating member, where the applicating member is separated from the body part of the instrument, FIG. 15 shows a detail of the applicating member and a sheet of surgical material, FIG. 19 shows an assembly of the third preferred embodiment of the instrument, FIG. 20 shows a first sleeve member according to the invention suited for fitting in a trocar, FIG. 21 shows an assembly of the third preferred embodiment of the instrument, where the first sleeve member is removed, FIG. 22 shows the third preferred embodiment of the instrument, where the applicating member is separated from the body part of the instrument.

DETAIL OF THE INVENTION

Figure 16:
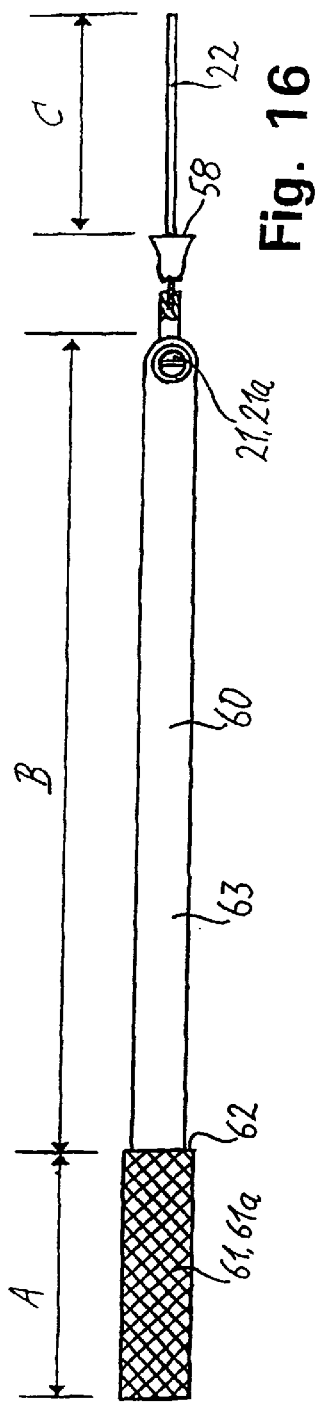
FIG. 16 is a diagrammatic top view illustrating the second preferred embodiment of the instrument according to the invention.
Figure 17:
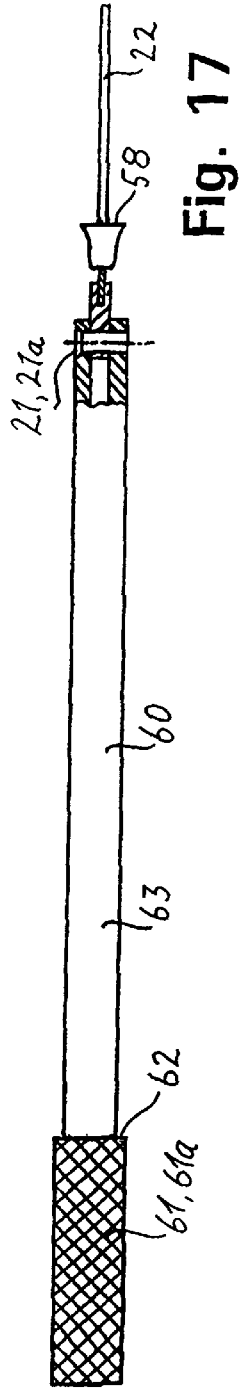
FIG. 17 is a diagrammatic side view illustrating the second preferred embodiment of the instrument.
Figure 18:
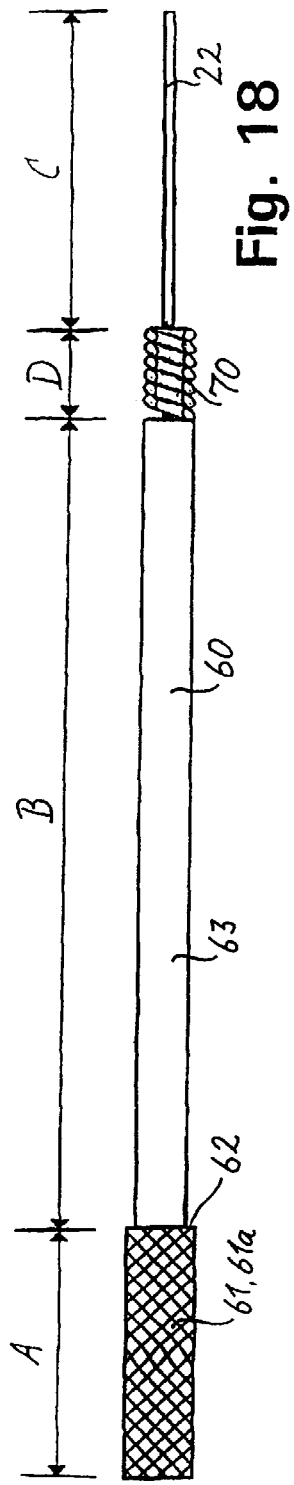
FIG. 18 is a diagrammatic illustration of a third preferred embodiment of an instrument according to the invention.

FIG. 1 shows a first preferred embodiment of an instrument 1 according to the invention. The instrument 1 comprises a sleeve member or a first sleeve member 15, shown in FIGS. 3, 12 and 20, and a body assembly 2, shown in FIG. 2. The body assembly 2, shown in FIG. 2, comprises a second sleeve member or sleeve member 6, shown in FIG. 5, and an inner assembly 11 and an applicating member 20 pivotally connected to the inner assembly 11 at the distal end of the inner assembly. A unit comprising the body assembly 2 except the applicating member is referred to as an elongated unit (not shown separately in the drawings).

The second sleeve member 6 shown in FIG. 5 has at least a first portion 6a at its proximal end and a second portion 6b at its distal end, the second portion 6b having a reduced diameter compared to the first portion 6a. At the cross sectional extension between the first and second portion, an abutment surface 7 is formed. An inner bore 8 extends in a longitudinal direction through the second portion 6b and through at least part of the first portion 6a, so as to allow at least part of the inner assembly shown in FIG. 4 to extend through at least the second portion 6b and to engage with control means comprised in the first portion 6a. The control means comprises a spring loaded button 4 and a roll 5. The roll 5 is engaged in the hollow part of the first portion 6a by bearing means (not shown). Preferably, the bearing means allow a smooth running of the roll 5.

Preferably, at least part of the first portion 6a of the second sleeve member 6 forms a handle 3, The handle 3 may have any cross sectional shape. In a preferred embodiment of the invention, the cross section of the handle is circular over its upper and lower part 3a and linear over its right and left part, so as to form a pleasant and secure handle for the operator.

The inner assembly 11, shown in FIG. 4, comprises a shaft 27 having means 30 and 31 at its proximal end allowing the assembly to be received in corresponding means comprised in the roll 5. The edged portion 30 of the shaft 27 fits the inner shape of the roll 5, whereby the rotating motion of the roll 5 will be followed by the shaft 27. A pointed knob 31 at the proximal end of the shaft 27 allows the shaft 27 and thereby the inner assembly 11 to be secured in the second sleeve member 6. When assembling the inner assembly 11 and the second sleeve member 6, the pointed knob 31 will press against a sleeve mounted on a spiral spring (not shown) connected to the button 4. When the knob has completely passed the spring loaded sleeve, the spring load will press the sleeve against an intermediate part 32 of the shaft 27. At the same time, a knob 10 formed on the inner assembly at its distal end, will engage with a corresponding groove 9 at the distal end of the second sleeve member 6, thereby both fixing the inner assembly radially. As the spring loaded sleeve abuts an abutment surface 31a on the pointed knob 31, the inner assembly will also be fixed in the longitudinal direction. The inner assembly is separated from the second sleeve member by pressing the button 4, whereby the spring loaded interconnection is relieved. The example of an interconnection and retaining configuration described above covers a first preferred embodiment of the invention. Obviously, many other configurations are possible, including other types of spring loaded locking mechanism, screw loaded mechanisms and magnetic interlocking systems.

Though in the first preferred embodiment of the invention, the rotating movement of the shaft 27 is activated by hand, it could also be activated by other means, e.g., an electromotor.

The inner assembly further comprises force transmission means for transmitting and transforming the rotating movement of the roll 5 into a rotating movement of the applicating member 20 around its pivot. The force transmission means comprise a threaded spindle 28 (FIG. 4) serially connected to the shaft 27. Preferably, the threaded spindle is formed on the shaft 27 itself. The shaft may be surrounded by an outer, stationary part 42, which is stabilised in relation to the shaft 27 by a preferably flexible muff 29. As shown in FIGS. 6, 9 and 10, the threaded spindle 28 of the shaft 27 is divided into two portions 28a and 28b, wherein one of them has a right-handed thread, and wherein the other has a left-handed thread. In the preferred embodiment of the invention, the first portion 28a is provided with a left-handed thread and the second portion with a left-handed thread. A displaceable or nut-like member 40, 41 is mounted on each portion of the spindle 28. Each of the nuts has an inner thread fitting the outer thread of the corresponding portion of the spindle. In the example shown in the figures, the nut 40 thus has a left-handed inner thread and the nut 41 has a right-handed inner thread. A wire or cable 46 is stretched between the two nuts, as shown clearly in FIGS. 8, 9 and 10. The wire extends from the first nut to the second nut around a pivot 21 of the applicating member 20, where it engages with the applicating member 20, and where it forms at least one closed loop around the pivot 21, which in a preferred embodiment comprises a screw or bolt 21a. A pivot pawl 21c extends through a hinge sleeve 21b comprised in a contact member 25. The pivot pawl 21c may preferably be formed from a portion of the screw 21a. In order to obtain a safe engagement of the wire 46 with the hinge sleeve 21b, the wire is guided through a bore 21c extending perpendicular to the longitudinal direction of the instrument 1 through the hinge sleeve 21b. The nuts are radially fixed in the outer, stationary part 42, whereby any rotation of the roll 5 and thus of the shaft 27 and the spindle 28 will result in a linear movement of the nuts 40 and 41 due to the tension in the wire 46. As the nuts are mounted on contrary directed threads, they will either move toward each other or from each other, when the shaft 27 is being rotated, while one of them will pull the wire 46, whereby the wire will always be subjected to tension. As the wire forms a closed loop around the pivot 21, the linear movement of the wire will result in a pivoting movement of the applicating member around the pivot 21.

The transmitting mechanism described above is also referred to as a Bowden cable.

The interconnection between the wire and the nuts may be obtained by mechanical means, such as a screw or spring pressing the wire against the nut material, by gluing, welding or soldering, by friction or by providing the free ends of the wire with a knob abutting the back surface of each of the nuts.

As illustrated by an arrow 45 in FIGS. 6 and 10, the applicating member may pivot at an angle of up to about 135° to each side from its straight position, when the roll 5 is rotated as indicated by an arrow 40. The angular range of the pivoting movement may be controlled by a stopping means or knob 26, which allows the applicating member 20 to pivot until the knob 26 hits the distal part 43 of the inner assembly. The rotating movement of the rotatable part 25 of the applicating member about its longitudinal axis is indicated by an arrow 35 in FIGS. 4 and 10.

The above description covers a preferred embodiment of the invention. Obviously, other embodiments are possible, including embodiments, wherein the force transmitting means comprise a toothed wheel and/or a worm wheel.

As shown in FIGS. 3, 4 and 6, the applicating member 20 preferably comprises a rod-shaped portion 22 provided with a slit 23 for retaining a sheet of surgical sheet material 50 such as TachoComb®, as illustrated in FIG. 7. At its proximal end it may have an outer part 25 comprising a cavity 24 for receiving one end of a roll of a sheet of surgical material rolled around the rod-shaped part 22, also referred to as sheet holding means. Preferably the outer part 25 is rotatably mounted on the contact member 25a.

The first sleeve member 15 comprises an inner bore 16 extending through the first sleeve member. At its proximal end, the first sleeve member has a portion 17 with an increased outer diameter, which preferably comprises a trumpet-shaped portion 18. The outer surface of the straight portion 19 of the first sleeve member 15 is suited for going through a trocar during surgical intervention. The inner diameter of at least part of the trumpet-shaped part of the first sleeve member preferably increases towards the terminal surface so as to from an abutment surface for abutting the abutment surface 7 of the second sleeve member 6.

Though in the preferred embodiments of the invention, the cross section of the first sleeve member shown in FIG. 3 is circular, it should be understood that the cross section can have both polygonal and/or any curved shapes.

Prior to performing a surgical intervention using an instrument according to the invention, a sheet of surgical material 50 is rolled around the rod-shaped portion 22 of the applicating member. An edge of the sheet is introduced into slit 23 in the rod-shaped portion of the applicating member, and is then rolled around the rod-shaped portion 22.

During minimally invasive surgical intervention, the first a sleeve member 15 is inserted into the body of a patient through a trocar. The body assembly 2 is then inserted into the body of the patient through the bore 16 of the first sleeve member 15. The radial extension of the bore 16 adjacent to the proximal end of the first sleeve member 15 provides a funnel for easy introduction of the applicating member with a sheet of surgical material rolled up thereon. The unrolling of the sheet of surgical material 50 is preferably performed by catching the surgical material with one or more forceps and unrolling the surgical material, whereby the outer part 25 and the rod-shaped part 22 of the applicating member will rotate relative to the stationary part 25a.

When an instrument according to the invention is used during normal surgery, where no trocar is present, an instrument according to the invention can be used without the first sleeve member 15.

The surface of the bore 16 and/or the outer surface of the second portion 6b of the sleeve member 6 may be provided with at least one and preferably with at least two 0-rings received in grooves in the respective surfaces. Thereby it is avoided that any gas or liquid may ooze out of the body of the patient through the surgical opening, e.g., during lung or abdomen surgery. This or any other kind of proofing arrangement will create friction between the assembly 2 and the first sleeve member 15. An effect thereof, which might be an advantage in some cases is that the operator will have to apply force in order to move the assembly 2 through the bore 16 of the first sleeve member 15, whereby a more accurate control of the instrument in its longitudinal direction may be obtained. This applies also for a second and third embodiment of the invention described below. Obviously, in the second and third embodiment of the invention, the 0-ring a or 0-rings may be received either in grooves in the surface of the bore 16 or in grooves in the outer surface of second portions 63 of a rod-shaped member 60 (FIGS. 13 and 21).

The dimensions A, B and C indicated in FIG. 10 may vary, and no restrictions concerning these instruments exist. However, for children surgery it is desired to reduce the length and the diameter of the instrument. In preferred embodiments of the instrument, the dimensions normally are as follows:

20 mm<A<60 mm, 220 mm<B<310 mm, 20 mm<C<80 mm, while their ratios preferably are as follows:

0.06<A/B<0.3, 0.25<A/C<3, 2.75<B/C<15.5

In a specific embodiment of the invention, the dimensions are chosen as:

A=40 mm, B=265 mm, C=48 mm, so that:

A/B=0.15, A/C=0.83, B/C=5.52.

The diameters of the rod-shaped parts preferably vary within any range relevant for surgical interventions. Normally, the following ranges are suitable:

Diameter d22 of the rod-shaped portion 22 of the applicating member: 1 mm<d22<8 mm Diameter d3a of the circular portion 3a of the handle: 10 mm<d3a<20 mm Outer diameter d19 of the straight portion of the first sleeve member: 6 mm<d19<14 mm In a specific embodiment of the invention, the diameters are chosen as:

d22=4 mm, d3a=15 mm, d19=10 mm.

Turning now to a second preferred embodiment of an instrument 56 according to the invention, FIG. 11 shows an assembly of the instrument. The instrument 56 comprises a sleeve member or a first sleeve member 15, shown in FIG. 3, 12 and 20, and a body assembly 57, shown in FIG. 13. The body assembly 57, shown in FIG. 13, comprises an elongated, preferably rod-shaped member 60 and an applicating member 20 pivotally connected to the distal part 43 of an elongated unit (not shown separately in the drawings). The elongated unit comprises the rod-shaped member 60 and the proximal part 43 of the applicating member.

In a preferred embodiment shown in FIGS. 11, 13, 14, 15, 16 and 17, a substantially plane surface 58 is formed at the proximal and the distal end of the rotatable member 25 so as to protect the surgical material. In an alternative embodiment of the invention, the surface 58 is substituted by a rod-shaped member having a cavity to receive one end of a roll of a sheet of surgical material.

The above description of the applicating member 20 and the first sleeve member 15 including the general remarks concerning these and any other parts and the entire instrument and its application also applies to the second preferred embodiment of the instrument.

The rod-shaped member 60, shown in FIG. 14, has at least a first portion 61 at its proximal end and a second portion 63 at its distal end, the second portion 63 having a reduced diameter compared to the first portion 61. At the cross sectional extension between the first and second portion, an abutment surface 62 is formed. An inner bore 64 extends in a longitudinal direction into the second portion 63 through at least part of the second portion. At least the distal end of the bore 64 is provided with an inner thread suited for engaging an outer thread 66 on a rod-shaped portion the distal part 43 of the elongated unit, so as to enable the instrument to be separated, e.g, for cleaning purposes.

Preferably, at least part of the first portion 61 of the rod-shaped member 60 forms a handle 61a. The handle 61a may have any cross sectional shape. In a preferred embodiment of the invention, the cross section of the handle is circular. However, the cross section may have any other shape, including the shape of the first preferred embodiment of the invention, described above. The abutment surface 62 is suited for abutting the abutment surface comprised in the bore of the first sleeve member, which is described in detail above.

As illustrated by an arrow 45 in FIG. 14, the applicating member may pivot at an angle of up to about 135° to each side from its straight position. The angular range of the pivoting movement may be controlled by a stopping means or knob 26, which allows the applicating member 20 to pivot around its pivot 21 until the knob 26 hits the distal part 43 of the elongated unit. The rotating movement of the rotatable part 25 of the applicating member about its longitudinal axis is indicated by an arrow 35 in FIG. 13.

The pivoting movement of the applicating member 20 may be activated by hand using other tools, e.g., forceps. The force needed to activate the pivoting movement is determined by the distortion of a tension bolt 21a, shown in FIGS. 16 and 17.

The dimensions A, B and C indicated in FIG. 16 may vary as described above in relation to the first preferred embodiment of the instrument. Suitable ranges of absolute and relative dimensions as well as the more preferred values of A, B and C as well as the diameters of the rod-shaped members are identical to those indicated in the above description concerning the first preferred embodiment of the invention.

FIGS. 18, 19, 20, 21 and 22 illustrate a third embodiment of the invention. The instrument 75 comprises a sleeve member or a first sleeve member 15, shown in FIGS. 3, 12 and 20, and a body assembly 76, shown in FIG. 21. The body assembly 76, comprises an elongated, preferably rod-shaped member 60 and an applicating member 20 pivotally connected by means of a spiral spring 70 to the distal part 43 of an elongated unit (not shown separately in the drawings). The elongated unit comprises the rod-shaped member 60 and the proximal part 43 of the applicating member.

The above description of the applicating member 20 and the first sleeve member 15 including the general remarks concerning these and any other parts and the entire instrument and its application also applies to the third embodiment of the instrument. Further, the above description of the rod-shaped member 60 applies to the third embodiment of the instrument.

The spiral spring 70 establishes a pivotable link between the applicating member 20 and the rod-shaped member 60. The spiral spring allows the applicating member 20 to pivot in any direction into a position, where the free end of the rod-shaped portion 22 of the applicating member hits the rod-shaped member 60, or into any intermediate position. The pivoting movement of the applicating member 20 may be activated by hand using other tools, e.g., forceps. The force needed to activate the pivoting movement of the spring 70 is determined by its spring constant.

In a preferred embodiment shown in FIGS. 18, 19, 21 and 22, a substantially plane surface 58 is formed at the proximal and the distal end of the spring so as to protect the surgical material from the spring material. In an alternative embodiment of the invention, the surface 58 is substituted by a rod-shaped member having a cavity to receive one end of a roll of a sheet of surgical material. Further, the rod-shaped portion of the applicating member may be rotatably mounted in relation to the spring 70.

In an alternative embodiment of the invention, the rod-shaped part of the spiral may is formed from the free end portion of the spring wire material.

In other embodiments of the invention, the spiral spring is substituted by any elastic member, e.g., a solid member made from a resilient material.

The dimensions A, B and C indicated in FIG. 16 may vary as described above in relation to the first preferred embodiment of the instrument. Suitable ranges of absolute and relative dimensions as well as the more preferred values of A, B and C as well as the diameters of the rod-shaped members are identical to those indicated in the above description concerning the first preferred embodiment of the invention. The dimension D normally varies within the following range:

$$2 \text{ mm} < D < 20 \text{ mm}$$

while its ratio to the other dimensions preferably is as follows:

$$1 < A/D < 30$$

In a specific embodiment of the invention, the dimension D is chosen as:

$$D = 12 \text{ mm}$$

so that:

$$A/D = 3.33,$$

for A=40 mm. The dimension B and C as well as the diameters of the rod-shaped preferably vary within the above mentioned ranges.

The three embodiments of the instruments according to the invention are preferably made from medical certified steel, including stainless steel. Other materials suitable for medical application would be plastics, teflon or titanium or combinations thereof. Some parts may be made from hardened plastic, e.g., the bearing parts of the applicating member. Some parts, e.g., the wire material may also be made from special materials, e.g., titanium so as to reduce wear.

What is claimed is:

1. An instrument for the application of surgical sheet material and comprising
    an elongated unit,
    a sheet material applicating member pivotally connected to the distal end of an elongated rod member comprised in the elongated unit, so as to allow movement of the applicating member relative to the elongated unit,
    manoeuvring means for the pivotal movement of the applicating member,
    operating means operating the manoeuvring means and being positioned at the proximal end of the elongated unit, the operating means comprising a rotatably mounted adjustment member and being connected to the applicating member through force transmission means comprising:
        a spindle which is mounted rotatably about its longitudinal axis and coextend with the rod member, and which has first threads formed thereon, and
        at least a first longitudinally displaceable member defining second threads engaging with the first threads, the displaceable member being interconnected with the applicating member, whereby rotation of the spindle member causes displacement of the first displaceable member and a pivoting movement of the applicating member around its pivot at the distal end of the elongated unit, and whereby the applicating member may be retained in a desired angular position during surgical intervention.

2. An instrument according to claim 1, wherein the force transmission means further comprise third threads formed on the spindle, the first and third threads being right and left handed, respectively, or vice versa, and a second displaceable member defining fourth threads cooperating with the third threads and being interconnected with the applicating member.

3. An instrument according to claim 1 or 2, wherein the applicating member comprises a rod-shaped portion.

4. An instrument according to claim 3, wherein at least the rod-shaped portion of the applicating member defines a slit extending longitudinally over at least part of the length of the applicating member.

5. An instrument according to claims 1 or 2, further comprising a first sleeve member having a bore allowing the applicating member and at least the distal portion of the elongated unit to pass therethrough, the sleeve member being adapted to be received in a trocar during surgical intervention.

6. An instrument according to claim 5, wherein a radial abutment surface is defined within the bore of the first sleeve member for cooperating with a corresponding abutment surface defined on the elongated unit so as to allow easier control of the elongated unit during surgical intervention.

7. An instrument according to claim 6, wherein the abutment surface defined in the bore is an annular abutment surface having an inner diameter increasing in the direction of the proximal end of the sleeve member.

8. An instrument according to claim 7, wherein the annular abutment surface is positioned adjacent to the proximal end of the sleeve member.

9. An instrument according to claims 1 or 2, wherein the applicating member is pivotal about one axis only.

10. An instrument according to claim 5, wherein the applicating member is mounted on the elongated rod member, and further comprising a second sleeve member surrounding the rod member and having a handle formed at its proximal end.

11. An instrument according to claim 6, wherein the abutment surface of the elongated unit is formed at the distal end of the handle.

12. An instrument according to claims 1 or 2 wherein the operating means are releasably connected to the manoeuvring means.

13. An instrument according to claim 12, wherein the elongated rod member is mounted rotatably about its longitudinal axis in relation to the handle, the spindle being mounted on or forming part of the rod member.

14. An instrument according to claims 3, wherein at least the rod-shaped portion of the applicating member is mounted rotatably about its Longitudinal axis about a non-rotatable, proximal part of the applicating member.

15. An instrument for the application of surgical sheet material and comprising
an elongated unit comprising a shaft with a handle,
a sheet material applicating member pivotally connected to the distal end of the elongated unit, so as co allow movement of the applicating member relative to the elongated unit,
means for retaining the applicating member in a desired angular position during surgical intervention,
a sleeve member having a trumpet-shaped enlargement at its proximal end,
the interconnection between the elongated unit and the applicating member comprising a contact member, which is movably connected to the elongated unit, and which may pivot at an angle of up to about 135° to each side from its straight position, and which is connected to the elongated unit by means of a tension bolt, the contact member comprising connection means, which are guided through the elongated unit to the upper exterior of the proximal end of the elongated unit,
the applicating member with a stopping means and a sheet holding means being pivotally connected to the contact member.

16. An instrument according to claim 15, wherein the connection means comprise a toothed wheel or a worm wheel.

17. An instrument according to claim 15, wherein the connection means comprise a Bowden cable.

18. An instrument according to claim 15, wherein the connection means comprise a chain cable.

19. An instrument according to any of claims 15–18, wherein the elongated unit has at least a proximal and a distal portion, the cross section of the proximal portion being greater than the cross section of the distal portion, so that an abutment surface is formed, and the proximal portion forms a handle.

20. An instrument according to claim 19, wherein at least the rod-shaped portion of the applicating member is mounted rotatably about its longitudinal axis about a non-rotatable, proximal part of the applicating member.

21. An instrument for the application of surgical sheet material and comprising:
an elongated unit comprising a shaft with a handle,
a sheet material applicating member pivotally connected to the distal end of the elongated unit, so as to allow movement of the applicating member relative to the elongated unit, the interconnection between the elongated unit and the applicating member comprising a contact member, which may pivot at an angle of up to about 135° to each side from its straight position, the tensile strength of the hinge mechanism being determined by a tension bolt whereby the applicating member may be retained in a desired angular position during surgical intervention, the applicating member comprising a stopping means and a sheet holding means and being rotatably mounted on the contact member.

22. An instrument for the application of surgical sheet material and comprising
an elongated member,
a sheet material applicating member pivotally connected to the distal end of the elongated member,
wherein the elongated member has at least a first and a second portion, and wherein the second portion is surrounded by a sleeve member, and wherein the interconnection between the elongated member and the applicating member has an extension forming the applicating member, said extension being provided with a slit, the slit being suited for fastening a sheet of surgical material, the applicating member being pivotable at an angle of up to about 90° in any direction, the interconnection between the applicating member and the elongated member comprising a spiral spring.

23. An instrument according to claim 22, wherein the free end portion of the spiral spring forms at least part of the second elongated member.

24. An instrument according to claim 6, wherein the applicating member is mounted on the elongated rod member, and further comprising a second sleeve member surrounding the rod member and having a handle formed at its proximal end.

25. An instrument according to claim 7, wherein the applicating member is mounted on the elongated rod member, and further comprising a second sleeve member surrounding the rod member and having a handle formed at its proximal end.

26. An instrument according to claim 8, wherein the applicating member is mounted on the elongated rod member, and further comprising a second sleeve member surrounding the rod member and having a handle formed at its proximal end.

27. An instrument according to claim 9, wherein the applicating member is mounted on the elongated rod member, and further comprising a second sleeve member surrounding the rod member and having a handle formed at its proximal end.

28. An instrument according to claim 10, wherein the elongated rod member is mounted rotatably about its longitudinal axis in relation to the handle, the spindle being mounted on or forming part of the rod member.

* * * * *